United States Patent [19]

Obana

[11] Patent Number: 4,605,686
[45] Date of Patent: Aug. 12, 1986

[54] LATEX FOR IMMUNOSEROLOGICAL TESTS AND A METHOD FOR THE PRODUCTION OF THE SAME

[75] Inventor: Satoshi Obana, Osaka, Japan

[73] Assignee: Sekisui Kagaku Kogyo Kabushiki Kaisha, Osaka, Japan

[21] Appl. No.: 710,234

[22] Filed: Mar. 11, 1985

[30] Foreign Application Priority Data

| Mar. 13, 1984 | [JP] | Japan | 59-48447 |
| Mar. 13, 1984 | [JP] | Japan | 59-48448 |
| May 4, 1984 | [JP] | Japan | 59-89897 |
| Jun. 5, 1984 | [JP] | Japan | 59-115785 |

[51] Int. Cl.$^4$ .................. C08L 41/00; G01N 1/00
[52] U.S. Cl. .................. 523/105; 524/817; 524/836; 424/2
[58] Field of Search .......... 524/817, 836; 424/2; 523/105

[56] References Cited

U.S. PATENT DOCUMENTS

| 2,715,116 | 8/1955 | Hutchinson | 524/836 |
| 2,913,429 | 11/1959 | Floria et al. | 524/817 |
| 2,971,935 | 2/1961 | Floria | 524/817 |
| 3,436,187 | 4/1969 | Ferro et al. | 424/2 |
| 3,558,522 | 1/1971 | Louderback et al. | 424/2 |
| 4,071,670 | 1/1978 | Vanzo et al. | 524/836 |

FOREIGN PATENT DOCUMENTS

| 55-131008 | 10/1980 | Japan | 524/817 |
| 57-14610 | 1/1982 | Japan . | |
| 57-16011 | 1/1982 | Japan | 524/836 |
| 57-55908 | 4/1982 | Japan | 524/817 |
| 786146 | 11/1957 | United Kingdom | 524/817 |
| 946953 | 1/1964 | United Kingdom | 524/836 |

Primary Examiner—Joseph L. Schofer
Assistant Examiner—N. Sarofim
Attorney, Agent, or Firm—Spencer & Frank

[57] ABSTRACT

A latex for immunoserological tests containing polystyrene and/or polystyrene derivative particles which are prepared by polymerizing styrene and/or styrene derivatives in the absence of emulsifying agents, said particles having uniform diameters and a specific gravity of 1.05 or more.

20 Claims, No Drawings

LATEX FOR IMMUNOSEROLOGICAL TESTS AND A METHOD FOR THE PRODUCTION OF THE SAME

BACKGROUND OF THE INVENTION

1. Field of the invention

This invention relates to a latex for immunoserological tests and a method therefor.

2. Description of the prior art

Along with the progress in immunoserology, improvements in the techniques of clinical examinations are remarkable. In immunoserological examinations, test tubes are used, and for the dilution of the serum, measuring pipettes are employed. Both the complexity of the procedures of using such test tubes and pipettes, and the handling of large numbers of specimens caused by the increased numbers of examinations made, are factors in lowering the accuracy of immunoserological tests. However, with the introduction of automation into clinical examinations, as well as in the realm of immunoserology, the amount of blood taken from the patient has decreased, and the small-volume test method, or microtitration method, in which exact clinical data is obtained using small amounts of test reagents, is now being used. The microtitration method was proposed in 1955 by the Hungarian researcher Takatsy, and in 1962 the American worker Sever suggested improvements. In 1963 in the United States, a microtitration kit was made commercially available, and since then, this kit has been accepted and used for immunoserological tests all over the world. In 1967, the Center for Disease Control (CDC) in the United States adopted this kit as the standard test method for complement fixation reactions. The microtitration method is used in the training manual of the Public Health Service. This kit became known to workers in the field of virology in Japan relatively early, and the imported kits are being used in virus immunoserological examinations (hemagglutination reactions, hemagglutination inhibition reactions, complement fixation reactions, etc.) and in the culture of cells and tissues. The characteristics of the microtitration method are: (1) with only a small volume of serum, a number of different tests can be done, (2) the operating procedure is simple, and many specimens can be speedily diluted in a short time, (3) the method is economical, because compared to other existing methods, only small amounts of antigen, antiserum, reagents, and so on are used, (4) the whole reaction can be seen on one plate, and detailed evaluation of agglutination and hemolysis is easy, and (5) this method has the same sensitivity and accuracy as other existing methods, with excellent reproducibility as well. In the microtitration method, blood cells of relatively high specific gravity are used, such as those taken from the red blood cells of sheep or chickens. When these blood cells from animals are stored, the putrefaction and denaturation of the cells are rapid, and storage for long periods is not possible; also, because there are large individual differences in the cells, the scatter of the test values is wide, and accurate data are difficult to obtain. These and other problems exist with this method. In addition, blood cells themselves contain antigens, which react with the various antigens in the serum being tested, easily giving rise to ambiguous reactions as a result. As a substitute for these blood cells, synthetic latex has been used in recent years. For example, Japanese Laid Open Patent Publication No. 51-9716 discloses a synthetic latex reagent. This synthetic latex is made using a surfactant (an emulsifying agent). Other synthetic latex reagents using surfactants are also known. The usual method of their preparation is to mix together in water an anionic emulsifying agent, a non-ionic one, and a cationic one, and havig added both styrene monomer and an initiator that is soluble in water, to leave the mixture at an appropriate temperature for an appropriate period of time, preferably in an atmosphere without oxygen. In latex synthesized in this way, in general, part of the emulsifying agents used during polymerization are adsorbed onto the surface of the particles of the polystyrene latex, and part are chemically bonded there, with the remainder in the latex in the free state. An equilibrium between adhesion to and release from the surface of the particles of polystyrene latex is reached among these three states. For the production of polystyrene latex by the usual methods such as these, emulsifying agents are indispensible for the formation of stable latex. However, non-adsorbed, free emulsifying agents have an undesirable effect on the aforementioned agglutination reaction of antibody and antigen. In the manufacture of diagnostic reagents, first of all, polystyrene latex such as that described above is sensitized with antigens and antibodies. However, when latex containing emulsifying agents is used, agglutination occurs at this stage. Next, in using latex sensitized with antigen or antibody, the agglutination reaction of the latex will detect the corresponding antibody or antigen that will react with it; if serum containing the antibody or antigen to be detected is brought into contact with the sensitized latex, agglutination occurs. When serum that does not contain such antibody or antigen is brought into contact with the sensitized latex, agglutination will not occur. Nevertheless, with sensitized latex that contains free emulsifying agents, even if negative serum (without antibody or antigen) is brought into contact with it, agglutination will occur, and thus there is often a so-called non-specific agglutination reaction. It is possible to remove emulsifying agents from the latex with ion-exchange techniques or with dialysis, but if this were done, since as mentioned before there is an equilibrium between the emulsifying agents in the free state and those adsorbed onto the surface of the particles of latex, the equilibrium is disturbed, the stability of the latex is greatly damaged, and in practice the latex becomes unusable. Japanese Laid Open Patent Publication No. 57-14610 discloses a method to obtain latex using styrene without emulsifying agents being present, in which styrene is, along with persulfate, the starting materials for polymerization; after polymerization takes place in water, the mixture is made alkaline and heated, giving latex. Latex prepared in this way, when made into a reagent, will not cause non-specific agglutination reactions, because emulsifying agents are not used. Moreover, the stability of the latex is excellent. However, because this latex has a small specific gravity, when it is used as a reagent, when investigating the agglutination characteristics of a specimen, a long period of time is required. In order to obtain latex of high specific gravity, such substances as vinyltoluene, chlorostyrene, methyl methacrylate, vinylchloride, and vinylidene-chloride are polymerized or copolymerized. However, if, for example, chlorostyrene is chosen, since it is highly reactive, it is difficult to control the polymerization reaction. Because monomers remain in the resulting latex, there is an unpleasant odor.

SUMMARY OF THE INVENTION

The latex for immunoserological tests of this invention which overcomes the above-discussed disadvantages and other numerous drawbacks of the prior art, contains polystyrene and/or polystyrene derivative particles which are prepared by polymerizing styrene and/or styrene derivatives in the absence of emulsifying agents, said particles having uniform diameters having a coefficient of variation in the range of 5% or less within each batch and a specific gravity of 1.05 or more. The particles have a diameter in the range from 0.07 to 10 μm and a specific gravity ranging from 1.10 to 1.60.

A method for producing a latex for immunoserological tests of this invention which overcomes the above-discussed disadvantages of the prior art, comprises: (1) polymerizing styrene and/or styrene derivatives using a persulfate as an initiator in the absence of emulsifying agents to form a suspension of polymer particles, (2) subjecting said suspension to a heat-treatment under alkaline conditions, and (3) subjecting said suspension to a chlorination-treatment resulting in the particles having a specific gravity of 1.05 or more.

A method for producing the above-mentioned latex for immunoserological tests comprises: (1) copolymerizing styrene and styrenesulfonates using a persulfate as an initiator in the absence of emulsifying agents to form a suspension of copolymer particles, (2) subjecting said suspension to a heat-treatment under alkaline conditions, (3) subjecting said suspension to a heat-treatment under neutral or acidic conditions, and (4) subjecting said suspension to a chlorination-treatment. The polymerization is carried out in an aqueous solution containing divalent metal oxides or hydroxides. The heat-treatment under alkaline conditions is achieved at a temperature from 50° to 90° C. for 10 to 100 hours, and said heat-treatment under neutral or acidic conditions is achieved at a temperature from 60° to 80° C. for 10 to 50 hours. The chlorination-treatment is achieved at a temperature from 5° to 65° C. for 0.16 to 8.33 hours.

A method for producing the latex for immunoserological tests comprises: (1) polymerizing styrene using a persulfate as an initiator in the absence of emulsifying agents to form a suspension of polymer particles, (2) subjecting said suspension to a heat-treatment under alkaline conditions, and (3) subjecting said suspension to a chlorination-treatment. The heat-treatment under alkaline conditions is achieved at a temperature from 50° to 100° C. for 5 to 30 hours. The chlorination-treatment is achieved at a temperature from 5° to 65° C. for 0.5 to 50 hours.

A method for producing the latex for immunoserological tests comprises: (1) polymerizing styrene under weak alkaline conditions using a persulfate as an initiator in the absence of emulsifying agents to form a suspension of polystyrene particles, (2) subjecting said suspension to a heat-treatment under neutral or acidic conditions resulting in polystyrene particles containing crosslinked polystyrene, and (3) subjecting said polystyrene particles containing crosslinked polystyrene to a chlorination-treatment. The polymerization under weak alkaline conditions is carried out at a pH value from 7.1 to 7.8 at a temperature from 50° to 100° C. for 5 to 30 hours. The heat-treatment under neutral or acidic conditions is achieved at a pH value from 2.4 to 7.0 at a temperature from 50° to 100° C. for 5 to 30 hours. The chlorination-treatment is achieved at a temperature from 10° to 65° C. for 0.3 to 50.0 hours.

The invention described herein makes possible the objects of (1) providing a latex for immune agglutinations which has uniform size and excellent stability; (2) providing a soap-free latex for immune agglutination in which self-agglutination and non-specific agglutination problems seldom, if ever, arise so that anyone can easily employ it for an immune agglutination test and readily evalutate the agglutination; (3) providing a latex for immune agglutinations by which precise examination values can be obtained; (4) providing a latex for immune agglutinations having the desired particle size and the desired specific gravity; (5) providing a latex for immune agglutinations which can be adopted to an R-PHA (Reverse Passive Agglutination) method, because it has uniform particle size and a sufficient specific gravity to thereby make the judgement of an immune agglutinaiton easy; (6) providing a latex for immunoserological tests the particles of which can be used as a carrier in EIA (enzymeimmunoassay) and RIA (Radioimmunoassay) testing because they are superior in the absorbent properties to antigens and/or antibodies and can be readily separated from the liquid; (7) providing a latex for immune agglutinations which can be used as a substitute for sheep or chicken red blood cells in a microtitration method employing an R-PHA test or a PHA test because there is little difference in size between individual particles thereby minimizing the scatter of the test values; and (8) providing a method for producing the above-mentioned latex for immune agglutinations and/or immunoserological tests.

DESCRIPTION OF THE PREFERRED EMBODIMENTS

Latex

A latex for immunoserological tests contains polystyrene and/or polystyrene derivative particles which are prepared by polymerizing styrene and/or styrene derivatives in the absence of emulsifying agents. The particles have a diameter in the range from 0.07 μm to 10 μm; a coefficient of variation in the range of 5% or less, preferably 3% or less and more preferably from 2% to 0.5%; and a specific gravity of 1.05 or more, preferably from 1.05 to 1.60. The latex can be obtained as follows:

Polymer Latex Preparation

A latex for immunoserological tests of this invention can be prepared by polymerizing styrene using a persulfate as an initiator in the absence of emulsifying agents to form a suspension of polymer particles, subjecting said suspension to a heat-treatment under alkaline conditions, and subjecting said suspension to a chlorination-treatment.

Examples of a persulfate used as an initiator are the same as the above-mentioned. The ratio of persulfates to styrene is 8% by weight or less, preferably 0.09 to 6% by weight and more preferably 0.1 to 5% by weight. The polymerization of styrene is carried out within a reactor charged with water, and the resulting suspension of styrene polymers is heated at a temperature from 50° to 100° C., preferably 60° to 85° C. for 0.3 to 50 hours, preferably 5 to 30 hours under alkaline conditions (a pH value of 7.5–12.5, preferably 8.0–11.5) to decompose the persulfate initiator, followed by a chlorination-treatment at a temperature from 5° to 65° C., preferably 10° to 60° C. for 0.16 to 8.33 hours, preferably 0.5 to 6.66 hours and more preferably 1 to 6 hours thereby achieving a chlorination of the particles to an extent of 5 to 40%, preferably 10 to 30%.

Copolymer Latex Preparation

Styrene and styrenesulfonates are copolymerized using a persulfate as an initiator in the absence of emulsifying agents to form a suspension of copolymer particles; the suspension is subjected to a heat-treatment successively under alkaline conditions and neutral or acidic conditions; and then the suspension is subjected to a chlorination-treatment.

As a styrenesulfonate, for example, sodium styrenesulfonate, potassium styrenesulfonate, lithium styrenesulfonate, ammonium styrenesulfonate, etc. are used. The ratio of a styrenesulfonate to styrene is 3% by weight or less, preferably 0.0001 to 3% by weight and more preferably 0.001 to 2% by weight. Examples of a persulfate as an initiator are ammonium persulfate, potassium persulfate, sodium persulfate, etc. The ratio of a persulfate to the total weight of the styrene monomer is from 0.01 to 1% by weight. Divalent metals contained in the oxide or hydroxide forms that are prefered for copolymerization, but not specifically necessary to copolymerization, are, for example, Fe, Mg, Ca, Cu, etc. The ratio of divalent metal oxides or hydroxides to the styrene monomer is from 0.003 to 3.0% by weight.

The copolymerization of styrene with styrene-sulfonates is carried out within a reactor charged with water. The reaction time, although depending upon the kinds of styrene, styrenesulfonates and initiators, the concentration of divalent metal oxides or hydroxides, etc., is generally in a range from 5 to 50 hours. The resulting suspension of copolymer particles is then kept heated under alkaline conditions (a pH value of 7.5–12.5, preferably 8.0–11.0) at a temperature from 50° to 90° C., preferably 60° to 80° C., for 10 to 100 hours. The suspension is then kept heated under neutral or acidic conditions at a temperature from 60° to 80° C. for 10 to 50 hours followed by a chlorination-treatment at a temperature from 5° to 65° C., preferably 10° to 60° C. for 0.16 to 8.33 hours, preferably 0.5 to 6.66 hours and more preferably 1 to 6 hours thereby achieving a chlorination of the particles to an extent of 5 to 40%, preferably 10 to 30%.

If the treatment conditions deviate from the above-mentioned, a self-agglutination tends to arise in the resulting latex particles due to damage on the surface of each of the particles. Even though latex particles which suffer no damage can be obtained, their specific gravity is so great that they are sedimented too fast to be evaluated using a microtitration method. While the posibility of positive agglutination was great, only quasi-positive agglutination was observed and it was concluded that precise data cannot be obtained therefrom. When the resulting latex particles have a specific gravity ranging from 1.10 to 1.60, the latex can be adopted to a microtitration method. The specific gravity of the latex can be adjusted to the desired level depending upon the chlorination-treatment conditions, which are determined by experimental data for the expected specific gravity of latex particles. Latex particles having a great specific gravity obtained by a chlorination-treatment according to this invention are more sedimentary than conventional latex particles having a smaller specific gravity, so that they can be subjected to an immune agglutination test in the state that they have gathered in the lower portion of a reaction tube thereby allowing for quick determination of the positive or negative immune agglutination and allowing for adoption thereof to an R-PHA method.

According to this invention, divalent metal oxides or hydroxides are used for copolymerization as desired, the reasons for which are as follows:

(1) The particle size of the latex, which is obtained by copolymerization of styrene with styrenesulfonates in the absence of emulsifying agents (i.e., a soap-free system), will be uniform even if there is an increase in the ratio of initiator to the styrene monomer. However, a latex reagent prepared from the resulting latex is inferior in sensitivity due to the non-specific agglutination problem which tends to arise so that it is an unstable reagent. In order to prepare a latex reagent having a minimized non-specific agglutination, highly purified (i.e., highly activated) antibodies or antigens must be employed causing a need for more care in production control and an increase in the cost. (2) On the contrary, in the event that divalent metal oxides or hydroxides are used for copolymerization, they act as a core of each of the latex particles. Copolymers of styrene and styrenesulfonates surround the core to form a uniform particle which maintains a uniform dispersion state in the reaction system resulting in a latex containing particles of uniform shape and size. The particles range in diameter from 0.07 to 10 μm and have a CV value (the standard deviation of particle diameters/the average of particle diameters ×100) of 5% or less.

According to this invention, the suspension of copolymer particles is subjected to heat-treatments successively under alkaline conditions and neutral or acidic conditions, the reasons for which are as follows: A persulfate is employed as an initiator for copolymerization, resulting in a polymer chain having sulfates ($OSO_3^-$) at both ends thereof, thereby generating an electric repulsion between polymer chains so that the dispersion state of the latex will be stabilized. Such an electrical repulsion alone due to sulfate ions is not enough to maintain the latex in a stable dispersion state, but the addition of sulfonates to the polymer chains by copolymerization of styrenesulfonates is required to achieve a significantly stable dispersion. The latex used for immune agglutinations must be sensitive to an antigen-antibody reaction and have excellent agglutination; that is, the latex is usually maintained in a stable dispersion state and agglutinates sensitively by an antigen-antibody reaction. An index of such a dispersion state is represented by a $\zeta$-potential which indicates the degree of charges on the surface of each of the latex particles. The stability of the dispersion state of the latex is improved as the $\zeta$-potential is decreased. When the $\zeta$-potential is −60 mV or less, the dispersion state of the latex is extremely stabilized. However, within such a $\zeta$-potential range, the dispersion state is too stable to achieve a sensitive agglutination in an antigen-antibody reaction. In order to achieve a sensitive agglutination of the latex, $\zeta$-potential must be regulated to around −40 mV by, for example, the hydrolysis of sulfates to form carboxylates through hydroxylates. If the suspension of the above-mentioned copolymer particles is heated under alkaline conditions, sulfates therein become hydroxylates. The $\zeta$-potential in this reaction system cannot maintained at around −40 mV. Thus, the suspension is further heated under neutral or acidic conditions to convert hydroxylates to carboxylates thereby maintaining the $\zeta$-potential therein at around −40 mV, resulting in a latex which can effect an excellent agglutinating property.

Polymer Latex Preparation Under Weak Alkaline Conditions

A latex for immunoserological tests of this invention can be also prepared by polymerizing styrene under weak alkaline conditions using a persulfate as an initiator in the absence of emulsifying agents to form a suspension of polystyrene particles, subjecting said suspension to a heat-treatment under neutral or acidic conditions resulting in polystyrene particles containing crosslinked polystyrene, and subjecting said polystyrene particles containing crosslinked polystyrene to a chlorination-treatment.

Examples of persulfates are the same as the above-mentioned. The ratio of persulfates to styrene is 8% by weight or less, preferably 0.09 to 6% by weight and more preferably 0.1 to 5% by weight.

Styrene and an initiator are added to a reactor containing water, mixed and heated at a temperature from 50° to 100° C., preferably 60° to 85° C. for 5 to 35 hours under weak alkaline conditions of a pH value from 7.1 to 7.8 which is adjusted with hydroxides, oxides, carbonates, bicarbonates, etc. of alkali earth metals, examples of which are sodium hydroxide, potassium hydroxide, sodium carbonate, etc. to form a suspension of polystyrenes. The suspension is then heated at a temperature from 50° to 100° C., preferably 60° to 85° C. for 5 to 30 hours under neutral or acidic conditions of a pH value from 2.4 to 7.0, preferably 3.0 to 6.8, to partially promote a crosslinkage among polystyrenes. The polystyrenes containing crosslinked polystyrenes are then subjected to a chlorination-treatment at a temperature from 5° to 65° C., preferably 10° to 60° C. for 0.16 to 8.33 hours, preferably 0.5 to 6.66 hours and more preferably 1 to 6 hours to achieve a chlorination of the particles to an extent of 5 to 40%, preferably 10 to 30%, which varies, of course, depending upon the degree of crosslinkage of the latex particle and the particle size. The specific gravity of the resulting latex ranges from 1.06 to 1.50, preferably 1.10 to 1.50.

Each of the polystyrene particles, which has a partially crosslinked structure as mentioned above, has a high density of electric charges on the surface thereof, so that when it is subjected to a chlorination reaction, the reaction can be easily regulated resulting in a latex having the desired specific gravity. Thus, excessive chlorination is prevented so that the surface of each of the latex particles does not suffer damage. Since the resulting latex has a partially crosslinked structure, even though it is freeze-dried, the latex particles are neither damaged nor destroyed in freezing and/or redispersion so that there arises neither self-agglutination nor non-specific agglutination; for example, even an unstable latex which was prepared using *Streptococcus pyogenes* etc. can be stored for a long period of time by freeze-drying.

The control of polymerization and/or chlorination conditions allows preparation of uniform latex particles having the desired size and specific gravity, which are preferably applied to a microtitration method because problems due to non-specific agglutination do not arise.

EXAMPLE 1

(Preparation of copolymer latex)

A reactor was charged with 90 g of styrene monomer, 0.63 g of sodium styrenesulfonate, 10 g of magnesium hydroxide, 0.5 g of potassium persulfate and 450 g of an ion-exchanged water, nitrogen gas was then substituted for the air, followed by copolymerization maintaining a reaction temperature ranging from 70° to 72° C. for 24 hours. Upon completion of the copolymerization, air was substituted for the gas in the reactor. The resulting latex suspension, the pH value of which was adjusted to 8.6, was then subjected to heat-treatments successively at 70° C. for 20 hours under alkaline conditions and thereafter at 70° C. for 20 hours at pH 6.0. Then, the obtained latex was removed from the reactor, filtered with a filter paper (Toyo Filter Paper No. 2, 12.5 CM) and dried by a dryer at 70° C., resulting in a purified latex having a solid content of 13.8 (wt/wt)%. To a reactor having a capacity of 3 liters, 2,000 g of water and 500 g of a latex which was prepared to have a solid content of 10% by dispersing the above-mentioned dried latex particles into a distilled water were added and subjected to a chlorination-treatment with a chlorine gas at a temperature from 15° to 20° C. for 5.33 hours in a natural light. A nitrogen gas was then substituted for the atmosphere in the reactor for 2.5 hours. The chlorinated latex was removed from the reactor, filtered with a filter paper (Toyo Filter Paper No. 2, 12.5 CM), subjected to a dispersion-treatment with an ultrasonic wave for 1 minute, followed by dialysis in distilled water for 24 hours, resulting in a purified chlorination latex which had undergone a chlorination to an extent of 27,5% which was determined by an HCl analysis of the reaction suspension. It was observed by an electronmicroscope that the chlorinated latex particles have an average diameter of 0.71 $\mu$m, a CV value of as low as 1.6% and a specific gravity of 1.42.

(Evaluation of copolymer latex by an R-PHA test)

The polystyrene latex obtained in "Preparation of copolymer latex" in Example 1 was dispersed into a phosphate buffer solution (pH 7.4) to form a suspension having a solid content of 1%. On the other hand, HBs monospecific antibodies (which were purified by means of an affinity chromatography wherein the crude antibodies were passed twice through a Sepharose 4B column fixing HBs antigens therein) derived from a guinea pig, were dispersed into a phosphate buffer solution to form a solution having a concentration of 40 $\mu$g/cc.

One part by volume of the suspension (polystyrene latex) and 1 part of volume of the HBs monospecific antibodies were mixed and incubated at 37° C. for 1 hour to connect the antibodies to the latex, after which the treated latex was centrifuged at 18,000 r.p.m. for 8 minutes to eliminate free-antibodies. The resulting supernatant was subjected to a PHA (passive hemagglutination) test to determine an antibody value thereof and it was found that 99.5% or more of the used antibodies had been absorbed by the latex particles. The latex particles were then centrifuged at 18,000 r.p.m. for 8 minutes and re-dispersed into a phosphate buffer solution (pH 7.0) resulting in a latex reagent. The latex reagent was subjected to an R-PHA (reverse passive hemagglutination) test using an R-PHA kit which contained no sheep erythrocytes therein. The said kit was prepared using a REVERSECELL (an HBs antigen-detecting R-PHA kit manufactured by Yamanouchi Seiyaku).

Fifty microliters of a buffer solution were added to each of ten test tubes. To the first test tube was added 50 $\mu$l. of sample liquid containing HBs antigens with a concentration of 1 $\mu$g, and the sample was thoroughly mixed. A 50 $\mu$l portion of this mixture was taken and placed in the second test tube. The process was repeated until 10 samples were prepared giving dilution ratios to the samples of 1:2, 1:4, 1:8 . . . 1:1024. To each of the diluted sample liquids, 25 μl of the latex obtained in the above were added, shaken for 30 seconds and allowed to stand for 3 and 7 hours, respectively, followed by the evaluation of agglutinations thereof. These procedures were repeated three times. Table 1 shows the evaluation of agglutinations in which the mixtures of each of the diluted sample liquids and the latex were allowed to stand for 3 hours, and Table 2 shows the evaluation of agglutinations in which the mixtures were allowed to stand for 7 hours. For a reference standard a control R-PHA cell, i.e., a REVERSECELL, which was prepared by the absorption of HBs antibody in sheep erythrocytes instead of the latex, was used therefor. The results are also shown in Tables 1 and 2.

EXAMPLE 2

(Preparation of copolymer latex)

A reactor was charged with 90 g of styrene monomer, 0.20 g of sodium styrenesulfonate, 0.5 g of potassium persulfate and 450 g of an ion-exchanged water, nitrogen gas was then substituted for the air, followed by copolymerization maintaining a reaction temperature ranging from 70° to 72° C. for 24 hours. Upon completion of the copolymerization, air was substituted for the gas in the reactor. The resulting latex suspension was then subjected to heat-treatments successively at 70° C. for 20 hours under alkaline condition (pH 8.6) and thereafter at 70° C. for 20 hours at pH 6.0. Then, the obtained latex was removed from the reactor, filtered with a filter paper (Toyo Filter Paper No. 2, 12.5 CM) and dried by a dryer at 70° C., resulting in a purified latex having a solid content of 13.1 (wt/wt)%. To a reactor having a capacity of 3 liters, 2,000 g of water and 500 g of a diluted latex which was prepared to have a solid content of 10% by dispersing the above-mentioned dried latex particles into a distilled water were added and subjected to a chlorination-treatment with chlorine gas at a temperature ranging from 15° to 20° C. for 5.33 hours in a natural light. Nitrogen gas was then substituted for the gas in the reactor for 2.5 hours. The chlorinated latex was removed from the reactor, filtered with a filter paper (Toyo Filter Paper No. 2, 12.5 CM) and subjected to a dispersion-treatment with an ultrasonic wave for 1 minute, followed by dialysis in distilled water for 24 hours, resulting in a purified chlorinated latex which had undergone a chlorination to an extent of 17.4% which was determined by an HCl analysis of the reaction suspension. It was observed by an electromicroscope that the chlorinated latex particles had an average diameter of 0.67 μm, a CV value of as low as 0.7% and a specific gravity of 1.28.

(Evaluation of copolymer latex by an R-PHA test)

The polystyrene latex obtained in Example 2 was subjected to an agglutination test in the same manner as in Example 1. The results are shown in Tables 1 and 2.

TABLE 1

| An R-PHA test using copolymer latex (3 hours) | | | |
|---|---|---|---|
| Sample No. | Dilution Ratio | Latex in Example 1 | Latex in Example 2 | R-PHA Cell |
| 1 | 1:2 | +++ | +++ | +++ |
| 2 | 1:4 | +++ | +++ | +++ |
| 3 | 1:8 | +++ | ±±+ | ±++ |
| 4 | 1:16 | ±±± | --± | ±±± |
| 5 | 1:32 | --- | --- | ±±± |
| 6 | 1:64 | --- | --- | --- |
| 7 | 1:128 | --- | --- | --- |
| 8 | 1:256 | --- | --- | --- |
| 9 | 1:512 | --- | --- | --- |
| 10 | 1:1024 | --- | --- | --- |

Note:
—: no agglutination was observed
±: quasi-positive agglutination was observed
+: positive agglutination was observed
++: clearly positive agglutination was observed

TABLE 2

| An R-PHA test using copolymer latex (7 hours) | | | |
|---|---|---|---|
| Sample No. | Dilution Ratio | Latex in Example 1 | Latex in Example 2 | R-PHA Cell |
| 1 | 1:2 | +++ | +++ | +++ |
| 2 | 1:4 | +++ | +++ | +++ |
| 3 | 1:8 | +++ | ±±+ | +++ |
| 4 | 1:16 | ±±+ | --± | +++ |
| 5 | 1:32 | --± | --- | ±±± |
| 6 | 1:64 | --- | --- | --- |
| 7 | 1:128 | --- | --- | --- |
| 8 | 1:256 | --- | --- | --- |
| 9 | 1:512 | --- | --- | --- |
| 10 | 1:1024 | --- | --- | --- |

Note:
—: no agglutination was observed
±: quasi-positive agglutination was observed
+: positive agglutination was observed
++: clearly positive agglutination was observed The results indicate that the latex according to this invention seldom, if ever, has self-agglutination or non-specific agglutination problems since it is prepared in a soap-free system and is superior as to stability. Moreover, the latex particles have uniform size and sufficient specific gravity so that agglutination owing thereto can be readily evaluated. The latex particles do not influence determination of data in agglutination tests so that they can be adopted to a microtitration method.

Control 1

(Preparation of copolymer latex)

A reactor was charged with 90 g of styrene monomer, 0.63 g of sodium styrenesulfonate, 10 g of magnesium hydroxide, 0.5 g of potassium persulfate and 450 g of an ion-exchanged water, nitrogen gas was then substituted for the air, followed by copolymerization maintaining a reaction temperature ranging from 70° to 72° C. for 24 hours. Upon completion of the copolymerization, air was substituted for the gas in the reactor. The resulting latex suspension was heated successively at 70° C. for 20 hours at pH 8.6 and at 70° C. for 20 hours at pH 6.0. Thereafter, the obtained latex was removed from the reactor, filtered with a filter paper (Toyo Filter Paper No. 2, 12.5 CM) and dried by a dryer at 70° C., resulting in a purified latex having a solid content of 13.4 (wt/wt)%. It was observed by an electronmicroscope that the chlorinated latex particles have an average diameter of 0.695 μm, a CV value of 1.9% and a specific gravity of 1.03.

(Evaluation of copolymer latex by an R-PHA test)

The latex obtained in Control 1 was subjected to an agglutination test in the same manner as in Example 1.

Although the mixtures of each of the sample liquids containing HBs antigens and the latex were allowed to stand for 7 hours, no agglutination could be observed.

Control 2

(Preparation of polymer latex)

A reactor was charged with 90 g of styrene monomer, 2 g of a nonionic emulsifying agent (Trade name Emul Jet 49 manufactured by Daiichi Kogyo Seiyaku), 0.6 g of potassium persulfate and 450 g of an ion-exchanged water, nitrogen gas was then substituted for the air, followed by polymerization maintaining a reaction temperature ranging from 70° to 72° C. for 24 hours. It was observed by an electronmicroscope that the resulting latex particles have an average diameter of 0.725 μm and a CV value of as great as 12.7%. The specific gravity of the later was 1.04.

(Evaluation of polymer latex by an R-PHA test)

The latex obtained in Control 2 was subjected to an agglutination test, in the same manner as in Example 1, in which a non-specific agglutination was observed after the mixtures of each of the sample liquids containing HBs antigens and the latex were allowed to stand for 12 hours. Then, using the latex, a latex reagent was prepared in the same manner as in Example 1 and subjected to an agglutination test with respect to human serums containing HBs antigens with a variety of concentrations. The results are shown in Table 3.

TABLE 3

| An agglutination test using polymer latex obtained in Control 2 | | | | | |
|---|---|---|---|---|---|
| Concentration of HBs antigens in Human Erythrocytes | 10 μg/ml | 1 μg/ml | 100 ng/ml | 10 ng/ml | 1 ng/ml |
| Degree of Agglutination | ++ | − | + | + | − |

Note:
−: no agglutination was observed
±: quasi-positive agglutination was observed
+: positive agglutination was observed
++: clearly positive agglutination was observed Then, the same tests as mentioned above were carried out for normal human serum (three hundred discrete samples) containing HBs antigens with a concentration of 0.4 ng/cc or less that had been determined using a REVERSEIA (an HBs antigen-detecting EIA kit manufactured by Yamanouchi Seiyaku, Japan). Thirteen out of three hundred samples were positive and twenty one out of the three hundred samples were quasi-positive. These data indicate that the latex reagent prepared by the latex in Control 2 has a non-specific agglutination problem.

EXAMPLE 3

(Preparation of polymer latex)

A reactor was charged with 75 g of styrene monomer, 0.40 g of potassium persulfate and 450 g of an ion-exchanged water, nitrogen gas was then substituted for the air, followed by polymerization at a temperature from 68° to 72° C. for 28 hours. After the polymerization was completed, the pH value of the resulting latex suspension was adjusted to 8.5. The suspension was then kept heated at 70° C. for 24 hours at pH 8.5, removed from the reactor and filtered with a filter paper (Toyo Filter Paper No. 2, 12.5 CM), followed by a drying by means of a dryer at 70° C. resulting in a purified latex having a solid content of 12.1 (wt/wt)%. To a reactor having a capacity of 3 liters, 1,800 g of water and 430 g of the diluted latex which was prepared to have a concentration of 10% by diluting the above-mentioned purified latex with a distilled water, were added and subjected to a chlorination-treatment with chlorine gas at a temperature ranging from 25° to 27° C. for 2.66 hours in a light provided by a 100 w mercury-vapor lamp. A nitrogen gas was then substituted for the gas in the reactor. The chlorinated latex was filtered with a filter paper (Toyo Filter Paper No. 2, 12.5 CM), resulting in latex particles which had undergone a chlorination to an extent of 26.4% which was determined by a HCl analysis of the latex. The chlorinated latex particles have an average diameter of 0.49 μm and a CV value of as low as 0.9%. The specific gravity of the latex was 1.40.

(Evaluation of polymer latex by an R-PHA test)

The latex obtained in Example 3 was subjected to an R-PHA test in the same manner as in Example 1 except that agglutinations were evaluated after the mixtures of each of the sample liquids containing HBs antigens and the latex were allowed to stand for 4.5 and 7 hours, respectively. The results are shown in Table 4 (for 4.5 hrs.) and Table 5 (for 7 hrs.).

TABLE 4

| An R-PHA test using polymer latex (4.5 hours) | | |
|---|---|---|
| Sample No. | Dilution Ratio | Latex in Example 3 / R-PHA Cell |
| 1 | 1:2 | +++ / +++ |
| 2 | 1:4 | +++ / +++ |
| 3 | 1:8 | ±±+ / ±++ |
| 4 | 1:16 | − − − / ±±± |
| 5 | 1:32 | − − − / − − − |
| 6 | 1:64 | − − − / − − − |
| 7 | 1:128 | − − − / − − − |
| 8 | 1:256 | − − − / − − − |
| 9 | 1:512 | − − − / − − − |
| 10 | 1:1024 | − − − / − − − |

Note:
−: no agglutination was observed
±: quasi-positive agglutination was observed
+: positive agglutination was observed
++: clearly positive agglutination was observed

TABLE 5

| An R-PHA test using polymer latex (7 hours) | | |
|---|---|---|
| Sample No. | Dilution Ratio | Latex in Example 3 / R-PHA Cell |
| 1 | 1:2 | +++ / +++ |
| 2 | 1:4 | +++ / +++ |
| 3 | 1:8 | ±±± / +++ |
| 4 | 1:16 | − − − / ±±± |
| 5 | 1:32 | − − − / − − − |
| 6 | 1:64 | − − − / − − − |
| 7 | 1:128 | − − − / − − − |
| 8 | 1:256 | − − − / − − − |
| 9 | 1:512 | − − − / − − − |
| 10 | 1:1024 | − − − / − − − |

Note:
−: no agglutination was observed
±: quasi-positive agglutination was observed
+: positive agglutination was observed
++: clearly positive agglutination was observed The results indicate that, as discussed in Examples 1 and 2, the latex according to this invention seldom, if ever, has self-agglutination or non-specific agglutination problems since it is prepared in the absence of emulsifying agents, and it has an excellent stability. Moreover, the latex particles have uniform size and sufficient specific gravity so that agglutinations owing thereto can be readily evaluated. The latex particles, since they have no agglutination problems, do not influence determination of data in agglutination tests and therefore can be adopted to a microtitration method.

Control 3

(Preparation of polymer latex)

A latex was prepared in the same manner as in Control 2.

(Evaluation of polymer latex by an R-PHA test)

The latex obtained in Control 3 was subjected to an R-PHA test in the same manner as in Control 2 except that the latex treated with antibodies was centrifuged at 15,000 r.p.m. for 15 minutes to eliminate free-antibodies and the latex particles were then sedimented by a centrifugation at 15,000 r.p.m. for 15 minutes and that the mixtures of each of the sample liquids containing HBs antigens and the latex were allowed to stand for 4.5 and 7 hours, respectively. No agglutination could be observed. Then, the latex obtained in Control 3 was treated in the same manner as in Example 3 to prepare a latex reagent, which was then subjected to an agglutination test with respect to human serums containing HBs antigens with a variety of concentrations. The results are shown in table 6.

TABLE 6

| An agglutination test using polymer latex obtained in Control 3 | | | | | |
|---|---|---|---|---|---|
| Concentration of HBs antigens in Human Erythrocytes ($\mu$g/ml) | 10 | 1 | 0.1 | 0.01 | 0.001 |
| Degree of Agglutination | ++ | − | + | + | − |

Note:
−: no agglutination was observed
±: quasi-positive agglutination was observed
+: positive agglutination was observed
++: clearly positive agglutination was observed Then, the same tests as mentioned above were carried out for normal human serum (158 discrete samples) containing HBs antigens with a concentration of 0.4 ng/ml or less that had been determined using a REVERSEIA (an HBs antigen-detecting EIA kit manufactured by Yamanouchi Seiyaku, Japan). Twenty out of the 158 samples were positive and 27 out of the 158 samples were quasi-positive. These data indicate that the latex reagent prepared from the latex in Control 3 has a non-specific agglutination problem.

EXAMPLE 4

(Preparation of polymer latex under weak alkaline conditions)

A reactor was charged with 90 g of styrene monomer, 0.48 g of potassium persulfate and 470 g of an ion-exchanged water, nitrogen gas was then substituted for the air, followed by polymerization at a temperature ranging from 70° to 72° C. for 24 hours. The pH value of the reaction mixture was 7.5. After the polymerization was completed, the pH value of the resulting polystyrene latex suspension was adjusted to 6.3. The suspension was then kept heated at 70° C. for 24 hours at pH 6.3, removed from the reactor and filtered with a filter paper (Toyo Filter Paper No. 2, 12.5 CM), followed by a drying by means of a dryer at 70° C., resulting in a purified latex having a solid content of 12,6 (wt/wt)%. To a reactor having a capacity of 3 liters, 2000 g of water and 500 g of a diluted latex which was prepared to have a concentration of 7.0% by diluting the above-mentioned purified latex with distilled water, were added and subjected to a chlorination-treatment with chlorine gas at a temperature from 13° to 15° C. for 4.5 hours. Nitrogen gas was substituted for the gas in the reactor for 3 hours. The chlorinated latex was filtered with a filter paper (Toyo Filter Paper No. 2, 12.5 CM) and subjected to an ultrasonic wave-treatment for 30 seconds to be dispersed into water, followed by dialysis in distilled water for 24 hours. The resulting latex had undergone a chlorination to an extent of 14.7%. It was observed by an electronmicroscope that the latex particles had an average diameter of 0.48 $\mu$m, a CV value of as low as 0.5% and a specific gravity of 1.31. A part of unchlorinated polystyrene latex containing cross-linked polystyrene was weighed, dried at 70° C. for 5 hours and mixed with a certain amount of methyl ethyl ketone (MEK) in a test tube, after which the test tube was sealed. The mixture in the tube was heated at 90° C. for 48 hours in a silicone oil bath. The resulting MEK-insoluble cross-linked polystyrene fraction was dried at 70° C. for 8 hours and weighed. The proportion of gelatinization thereof was determined to be 8.1%.

(Evaluation of polymer latex by an R-PHA test)

The latex obtained in Example 4 was subjected to an R-PHA test in the same manner as in Example 3. The results are shown in Table 7 (for 4.5 hrs.) and Table 8 (for 7 hrs.).

TABLE 7

| An R-PHA test using polymer latex (4.5 hours) | | | | |
|---|---|---|---|---|
| Sample No. | Dilution Ratio | Latex in Example 4 | Latex in Example 5 | R-PHA Cell |
| 1 | 1:2 | +++ | +++ | +++ |
| 2 | 1:4 | +++ | +++ | +++ |
| 3 | 1:8 | ±±+ | ±+± | ±++ |
| 4 | 1:16 | −−− | −−± | ±±± |
| 5 | 1:32 | −−− | −−− | −−− |
| 6 | 1:64 | −−− | −−− | −−− |
| 7 | 1:128 | −−− | −−− | −−− |
| 8 | 1:256 | −−− | −−− | −−− |
| 9 | 1:512 | −−− | −−− | −−− |
| 10 | 1:1024 | −−− | −−− | −−− |

Note:
−: no agglutination was observed
±: quasi-positive agglutination was observed
+: positive agglutination was observed
++: clearly positive agglutination was observed

TABLE 8

| An R-PHA test using polymer latex (7 hours) | | | | |
|---|---|---|---|---|
| Sample No. | Dilution Ratio | Latex in Example 4 | Latex in Example 5 | R-PHA Cell |
| 1 | 1:2 | +++ | +++ | +++ |
| 2 | 1:4 | +++ | +++ | +++ |
| 3 | 1:8 | ±±± | ±++ | +++ |
| 4 | 1:16 | −−− | −±± | ±±± |
| 5 | 1:32 | −−− | −−− | −−− |
| 6 | 1:64 | −−− | −−− | −−− |
| 7 | 1:128 | −−− | −−− | −−− |
| 8 | 1:256 | −−− | −−− | −−− |
| 9 | 1:512 | −−− | −−− | −−− |
| 10 | 1:1024 | −−− | −−− | −−− |

Note:
−: no agglutination was observed
±: quasi-positive agglutination was observed
+: positive agglutination was observed
++: clearly positive agglutination was observed

EXAMPLE 5

(Preparation of polymer latex under weak alkaline conditions)

A reactor was charged with 75 g of styrene monomer, 0.40 g of potassium persulfate and 450 g of an ion-exchanged water, nitrogen gas was then substituted for the air, followed by polymerization at a temperature ranging from 70° to 72° C. for 30 hours at pH 7.3. After the polymerization was completed, the resulting latex suspension was kept heated at 70° C. for 28 hours at pH 6.0. The latex of polystyrene containing cross-linked polystyrene was removed from the reactor, filtered with a filter paper (Toyo Filter Paper No. 2) and dried by a dryer at 70° C., resulting in a purified latex having a solid content of 12.3 (wt/wt)%. To a reactor having a capacity of 3 liters, 1,800 g of water and 400 g of a diluted latex which was prepared to have a concentration of 10.0% by diluting the above-mentioned purified latex with distilled water, were added and subjected to a chlorination-treatment with chlorine gas at a temperature ranging from 25° to 27° C. for 2.66 hours under a 100 w mercury-vapor lamp. Nitrogen gas was then substituted for the gas in the reactor for 2.33 hours. The chlorinated latex was then filtered with a filter paper (Toyo Filter Paper No. 2) and subjected to an ultrasonic wave-treatment for 1 minute to be dispersed in water, followed by dialysis in distilled water for 24 hours. The resulting latex had undergone a chlorination to an extent of 25.2%. It was observed by an electronmicroscope that the latex particles had an average diameter of 0.50 μm and a CV value of as low as 0.8%. The specific gravity of the latex was 1.43. The proportion of gelatinization of the latex was 7.02%.

(Evaluation of polymer latex under weak alkaline conditions by an R-PHA test)

The polystyrene latex obtained in Example 5 was subjected to an R-PHA test in the same manner as in Example 4. The results are shown in Tables 7 and 8.

Tables 7 and 8 indicate that, since the latex of this invention is prepared in the absence of emulsifying agents and has a cross-linked structure in part, self-agglutination and non-specific agglutination problems seldom, if ever, arise and it has an excellent stability. Moreover, the latex particles have uniform size and sufficient specific gravity so that agglutinations owing thereto can be readily evaluated. The latex particles do not influence determination of data in agglutination tests so that they can be adopted to a microtitration method.

Control 4

(Preparatin of polymer latex under weak alkaline conditions)

A latex was prepared in the same manner as in Control 2.

(Evaluation of polymer latex by an R-PHA test)

The latex obtained in Control 4 was subjected to an agglutination test, in the same manner as in Control 3, in which no agglutinations could be observed. Then, using the latex in Control 4, a latex reagent was prepared in the same manner as in Example 4 and subjected to an agglutination test for human serums containing HBs antigens with a variety of concentrations. The volume of each of the latex reagents was 25 μl and the volume of each of the human serum samples was 100 μl. The results are shown in Table 9.

TABLE 9

| An agglutination test using polymer latex obtained in Control 4 | | | | | |
|---|---|---|---|---|---|
| Concentration of HBs antigens in Human Erythrocytes (μg/ml) | 10 | 1 | 0.1 | 0.01 | 0.001 |
| Degree of Agglutination | ++ | − | + | + | − |

Note:
−: no agglutination was observed
±: quasi-positive agglutination was observed
+: positive agglutination was observed
++: clearly positive agglutination was observed Next, the same tests as in Control 3 were carried out for normal human serum (158 discrete samples) containing HBs antigens with a concentration of 0.4 ng/ml or less that had been determined using a REVERSEIA (an HBs antigen-detecting EIA kit manufactured by Yamanouchi Seiyaku). Twenty out of the 158 samples were positive and 27 out of the 158 samples were quasi-positive.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A latex for immunoserological tests containing polystyrene and/or polystyrene derivative particles which are prepared by polymerizing styrene or copolymerizing styrene and styrenesulfonates in the absence of emulsifying agents to form a suspension of polymer particles, and chlorinating said suspension to form particles having uniform diameters and a specific gravity ranging from 1.10 to 1.60.

2. A latex for immunoserological tests according to claim 1, wherein said latex is used for immune agglutinations.

3. A latex for immunoserological tests according to claim 1, wherein said particles have a coefficient of variation in the range of 5% or less within each batch.

4. A latex for immunoserological tests according to claim 1, wherein said particles have a diameter in the range from 0.07 to 10 microns.

5. A method for producing a latex for immunoserological tests comprising:
   (1) polymerizing styrene or copolymerizing styrene and styrenesulfonates using a persulfate as an initiator in the absence of emulsifying agents to form a suspension of polymer particles,
   (2) subjecting said suspension to a heat-treatment under alkaline conditions, and
   (3) subjecting said suspension to a chlorination-treatment resulting in the particles having a specific gravity of 1.05 or more.

6. A method for producing a latex for immunoserological tests according to claim 5, wherein said latex is used for immune agglutinations.

7. A method for producing a latex for immunoserological tests according to claim 5, wherein said particles have a coefficient of variation in the range of 5% or less within each batch.

8. A method for producing a latex for immunoserological tests according to claim 5, wherein said particles have a diameter in the range from 0.07 to 10 microns.

9. A method for producing a latex for immunoserological tests according to claim 5, wherein said particles have a specific gravity ranging from 1.10 to 1.60.

10. A method for producing a latex for immunoserological tests according to claim 5, which comprises:
   (1) copolymerizing styrene and styrene-sulfonates using a persulfate as an initiator in the absence of emulsifying agents to form a suspension of copolymer particles,
   (2) subjecting said suspension to a heat-treatment under alkaline conditions,
   (3) subjecting said suspension to a heat-treatment under neutral or acidic conditions, and
   (4) subjecting said suspension to a chlorination-treatment.

11. A method for producing a latex for immunoserological tests according to claim 10, wherein said copolymerization is carried out in an aqueous solution containing divalent metal oxides or hydroxides.

12. A method for producing a latex for immunoserological tests according to claim 11, wherein said heat-treatment under alkaline conditions is achieved at a temperature from 50° to 90° C. for 10 to 100 hours, and said heat-treatment under neutral or acidic conditions is achieved at a temperature from 60° to 80° C. for 10 to 50 hours.

13. A method for producing a latex for immunoserological tests according to claim 10 or 11, wherein said chlorination-treatment is achieved at a temperature from 5° to 65° C. for 0.16 to 8.33 hours.

14. A method for producing a latex for immunoserological tests according to claim 5, which comprises:
   (1) polymerizing styrene using a persulfate as an initiator in the absence of emulsifying agents to form a suspension of polymer particles,
   (2) subjecting said suspension to a heat-treatment under alkaline conditions, and
   (3) subjecting said suspension to a chlorination-treatment.

15. A method for producing a latex for immunoserological tests according to claim 14, wherein said heat-treatment under alkaline conditions is achieved at a temperature from 50° to 100° C. for 5 to 30 hours.

16. A method for producing a latex for immunoserological tests according to claim 14, wherein said chlorination-treatment is achieved at a temperature from 5° to 65° C. for 0.5 to 50 hours.

17. A method for producing a latex for immunoserological tests according to claim 5, which comprises:
   (1) polymerizing styrene under weak alkaline conditions using a persulfate as an initiator in the absence of emulsifying agents to form a suspension of polystyrene particles,
   (2) subjecting said suspension to a heat-treatment under neutral or acidic conditions resulting in polystyrene particles containing crosslinked polystyrene, and
   (3) subjecting said polystyrene particles containing crosslinked polystyrene to a chlorination-treatment.

18. A method for producing a latex for immunoserological tests according to claim 17, wherein said polymerization under weak alkaline conditions is carried out at a pH value from 7.1 to 7.8 at a temperature from 50° to 100° C. for 5 to 30 hours.

19. A method for producing a latex for immunoserological tests according to claim 17, wherein said heat-treatment under neutral or acidic conditions is achieved at a pH value from 2.4 to 7.0 at a temperature from 50° to 100° C. for 5 to 30 hours.

20. A method for producing a latex for immunoserological tests according to claim 17, wherein said chlorination-treatment is achieved at a temperature from 10° to 65° C. for 0.3 to 50.0 hours.

* * * * *